United States Patent
Molesworth et al.

(10) Patent No.: US 11,817,197 B2
(45) Date of Patent: Nov. 14, 2023

(54) MEDICAL PUMP ELECTRONIC PAIRING WITH DEVICE

(71) Applicant: Quasuras, Inc., Escondido, CA (US)

(72) Inventors: Hugh Molesworth, San Diego, CA (US); Kevin Hughes, San Diego, CA (US); Marc Goldman, San Diego, CA (US); Pravin Pillai, Escondido, CA (US); Paul M. Diperna, Escondido, CA (US)

(73) Assignee: QUASURAS, INC., Escondido, CA (US)

(*) Notice: Subject to any disclaimer, the term of this patent is extended or adjusted under 35 U.S.C. 154(b) by 214 days.

(21) Appl. No.: 17/166,833

(22) Filed: Feb. 3, 2021

(65) Prior Publication Data
US 2021/0249113 A1    Aug. 12, 2021

Related U.S. Application Data

(60) Provisional application No. 62/971,807, filed on Feb. 7, 2020, provisional application No. 62/971,789, filed on Feb. 7, 2020.

(51) Int. Cl.
G08B 21/04    (2006.01)
G16H 20/17    (2018.01)
(Continued)

(52) U.S. Cl.
CPC ............ *G16H 20/17* (2018.01); *A61M 5/142* (2013.01); *A61M 5/172* (2013.01);
(Continued)

(58) Field of Classification Search
USPC ... 340/539.12, 539.21, 539.22, 539.153, 9.3, 340/551, 555, 566, 575, 691.6, 692
See application file for complete search history.

(56) References Cited

U.S. PATENT DOCUMENTS

| 4,594,058 A | 6/1986 | Fischell |
| 5,399,168 A | 3/1995 | Wadsworth et al. |

(Continued)

FOREIGN PATENT DOCUMENTS

| EP | 3165247 | 5/2017 |
| WO | WO 15/134526 | 9/2015 |

(Continued)

OTHER PUBLICATIONS

International Search Report and Written Opinion dated Oct. 18, 2018 in International Application No. PCT/US2018/40944, filed: Jul. 5, 2018 and published as: WO/2019/010324 on Jan. 10, 2019.
(Continued)

*Primary Examiner* — Daniel Previl
(74) *Attorney, Agent, or Firm* — Schmeiser Olsen & Watts LLP

(57) ABSTRACT

Systems and methods for wireless electronic communication between a medical apparatus and a remote electronic computing device comprise generating and outputting by the medical apparatus an output signal, including: encoding data in the output signal according to a predetermined characteristic of the output signal; receiving and decoding by the remote electronic computing device the encoded data in the output signal; and establishing a pairing between the medical apparatus and the remote electronic computing device.

8 Claims, 13 Drawing Sheets

(51) Int. Cl.
*G16H 40/67* (2018.01)
*A61M 5/172* (2006.01)
*G06F 21/62* (2013.01)
*A61M 5/142* (2006.01)

(52) U.S. Cl.
CPC ......... *G06F 21/6245* (2013.01); *G16H 40/67* (2018.01); *A61M 2205/3317* (2013.01); *A61M 2205/3553* (2013.01)

(56) References Cited

U.S. PATENT DOCUMENTS

| | | |
|---|---|---|
| 5,573,515 A | 11/1996 | Wilson et al. |
| 6,077,246 A | 6/2000 | Kullas et al. |
| 6,186,982 B1 | 2/2001 | Gross et al. |
| 6,620,138 B1 | 9/2003 | Marrgi et al. |
| 6,669,669 B2 | 12/2003 | Flaherty et al. |
| 6,742,992 B2 | 6/2004 | Davis |
| 7,500,962 B2 | 3/2009 | Childers et al. |
| 7,658,734 B2 | 2/2010 | Adair et al. |
| 7,789,849 B2 | 9/2010 | Busby et al. |
| 8,029,460 B2 * | 10/2011 | Rush ................ G16H 20/17 604/503 |
| 8,056,582 B2 | 11/2011 | DiPerna |
| 8,167,581 B2 | 5/2012 | Schneeberger et al. |
| 8,287,495 B2 | 10/2012 | Michaud et al. |
| 8,298,184 B2 | 10/2012 | DiPerna et al. |
| 8,408,421 B2 | 4/2013 | DiPerna |
| 8,448,824 B2 | 5/2013 | DiPerna |
| 8,545,440 B2 | 10/2013 | Patrick et al. |
| 8,573,027 B2 | 11/2013 | Rosinko et al. |
| 8,905,731 B2 | 12/2014 | Baron |
| 8,926,561 B2 | 1/2015 | Verhoef et al. |
| 8,939,928 B2 * | 1/2015 | Savoie ............... A61M 5/1723 604/65 |
| 8,986,253 B2 | 3/2015 | DiPerna |
| 9,211,377 B2 | 12/2015 | DiPerna et al. |
| 9,250,106 B2 | 2/2016 | Rosinko et al. |
| 9,295,779 B2 | 3/2016 | Kamen et al. |
| 9,675,756 B2 | 6/2017 | Kamen et al. |
| 9,737,656 B2 | 8/2017 | Rosinko |
| 10,010,674 B2 | 7/2018 | Rosinko et al. |
| 10,213,546 B2 | 2/2019 | Anderson et al. |
| 10,279,106 B1 | 5/2019 | Cook et al. |
| 11,464,899 B2 * | 10/2022 | Searle .................. G16H 40/63 |
| 2002/0004643 A1 | 1/2002 | Carmel et al. |
| 2004/0257413 A1 | 12/2004 | Anderson et al. |
| 2005/0119611 A1 | 6/2005 | Marano-Ford et al. |
| 2005/0214129 A1 | 9/2005 | Greene et al. |
| 2008/0051716 A1 | 2/2008 | Stutz |
| 2008/0092969 A1 | 4/2008 | DiPerna |
| 2009/0030366 A1 | 1/2009 | Hochman |
| 2010/0145303 A1 | 6/2010 | Yodfat et al. |
| 2010/0185322 A1 | 7/2010 | Bylsma et al. |
| 2010/0232992 A1 | 9/2010 | Gray |
| 2011/0021993 A1 | 1/2011 | Bar-Haim et al. |
| 2011/0098638 A1 | 4/2011 | Chawla et al. |
| 2011/0118694 A1 | 5/2011 | Yodfat et al. |
| 2011/0186177 A1 | 8/2011 | Lanier, Jr. et al. |
| 2013/0055889 A1 | 3/2013 | Herz et al. |
| 2013/0150824 A1 | 6/2013 | Estes et al. |
| 2013/0237947 A1 | 9/2013 | Amirouche et al. |
| 2014/0134561 A1 * | 5/2014 | Smith .................. A61B 5/1118 600/595 |
| 2014/0228762 A1 | 8/2014 | Capone et al. |
| 2014/0276422 A1 | 9/2014 | Reilly et al. |
| 2014/0378903 A1 | 12/2014 | Quinlan |
| 2015/0106113 A1 | 4/2015 | Reddy |
| 2015/0273201 A1 | 10/2015 | Tallarida et al. |
| 2015/0290445 A1 | 10/2015 | Powers et al. |
| 2016/0038675 A1 | 2/2016 | Estes et al. |
| 2016/0129178 A1 | 5/2016 | Askarinya et al. |
| 2016/0361489 A1 | 12/2016 | Di Perna |
| 2017/0128709 A1 | 5/2017 | Chen |
| 2017/0203030 A1 * | 7/2017 | Brewer ............ A61M 5/14244 |
| 2017/0246380 A1 * | 8/2017 | Rosinko ........... A61M 5/14244 |
| 2018/0001000 A1 | 1/2018 | Herwig et al. |
| 2019/0009023 A1 | 1/2019 | Di Perna et al. |
| 2020/0030529 A1 | 1/2020 | Di Perna et al. |
| 2020/0214625 A1 | 6/2020 | Hooven et al. |
| 2021/0084700 A1 * | 3/2021 | Daniels ................. H04W 12/50 |
| 2022/0092960 A1 * | 3/2022 | Arumugam ............ H04W 4/80 |

FOREIGN PATENT DOCUMENTS

| | | |
|---|---|---|
| WO | WO 17/194074 | 11/2017 |
| WO | WO 19/010324 | 1/2019 |
| WO | WO 21/113537 | 6/2021 |
| WO | WO 21/113538 | 6/2021 |
| WO | WO 22/076337 | 4/2022 |

OTHER PUBLICATIONS

International Search Report and Written Opinion dated Jul. 31, 2015 in International Application No. PCT/US2015/18525 filed: Mar. 3, 2015 and published as: WO/2015/134526 on: Sep. 11, 2015.
International Search Report and Written Opinion dated Oct. 4, 2019 in International Application No. PCT/US2019/43146 filed: Jul. 24, 2019.
Office Action dated Jan. 2, 2020 in U.S. Appl. No. 15/122,132, filed Aug. 26, 2016 and published as: 2016/0361489 on Dec. 15, 2016.
Final Office Action dated Jun. 26, 2020 in U.S. Appl. No. 15/122,132, filed Aug. 26, 2016 and published as: 2016/0361489 on Dec. 15, 2016.
Office Action dated Nov. 16, 2020 in U.S. Appl. No. 16/028,256, filed Jul. 5, 2018 and published as: 2019/0009023 on Jan. 1, 2019.
Invitation to Pay Additional Fees dated: Feb. 23, 2021 in International Application No. PCT/US2020/63152 filed: Dec. 3, 2020.
International Preliminary Report on Patentability dated Jan. 26, 2021 in International Application No. PCT/US2019/43146 filed: Jul. 24, 2019.
Supplementary European Search Report dated Mar. 12, 2021 in European Patent Application No. EP 18828123.2 filed: Jul. 5, 2018.
International Search Report and Written Opinion dated Apr. 28, 2021 in International Patent Application No. PCT/US2020/63152 filed: Dec. 3, 3030.
International Preliminary Report on Patentability dated May 17, 2022 in International Patent Application No. PCT/US2020/63152 filed: Dec. 3, 2020.
Non-Final Office Action dated Dec. 1, 2022 in U.S. Appl. No. 17/111,396, filed Dec. 3, 2020 and published as: US2021/0170095 on Jun. 10, 2021.
Non-Final Office Action dated Apr. 26, 2023 in U.S. Appl. No. 17/111,402, filed Dec. 3, 2020 and published as: US/2021/0170094 on Jun. 10, 2021.
Final Office Action dated Apr. 14, 2023 in U.S. Appl. No. 17/111,396, filed Dec. 3, 2020 and published as: US2021/0170095 on Jun. 10, 2021.
International Search Report and Written Opinion dated Feb. 23, 2023 in International Patent Application No. PCT/US2022/045065 filed: Sep. 28, 2022 and published as: WO/2023/055819 on: Apr. 6, 2023.

* cited by examiner

MEDICAL PUMP ELECTRONIC PAIRING WITH DEVICE

RELATED APPLICATIONS

This application claims priority under 35 U.S.C. section 119(e) from U.S. Provisional Patent Application No. 62/971,789, filed Feb. 7, 2020, by Hugh Molesworth, et al., and entitled "Pump to Device Data Management", and from U.S. Provisional Patent Application No. 62/971,807, filed Feb. 7, 2020, by Hugh Molesworth, et al., and entitled "Pump to Device Pairing," the content of each of which is hereby incorporated by reference in its entirety.

BACKGROUND

Modern medical devices such as syringe or peristaltic-type pumps or other medical infusion devices typically require a user interface such as a display screen, buttons, activation switches, or other input/output devices to operate and control the pumps. With the emergence of improvements in computer technology, a need exists for a system to provide remote monitoring and control of medical pumps or the like. The delivery of therapeutic and non-therapeutic medical fluids is commonly performed intravenously (IV) or subcutaneously using a catheter or cannula and a syringe pump. However, a diabetic patient wearing an insulin delivery pump may require a remote practitioner such as a doctor or nurse to monitor and control the delivery of insulin to the patient and further may benefit from convenient, wireless monitoring and control of their own medical device.

SUMMARY

In one aspect, a method for wireless electronic communication between a medical apparatus and a remote electronic computing device comprises generating and outputting by the medical apparatus an output signal, including: encoding data in the output signal according to a predetermined characteristic of the output signal; receiving and decoding by the remote electronic computing device the encoded data in the output signal; and establishing a pairing between the medical apparatus and the remote electronic computing device.

In some embodiments, the medical apparatus includes an insulin delivery pump or other medical device and the remote electronic computing device includes a user interface and an input/output computing element for operating and controlling the insulin delivery pump or other medical device.

In some embodiments, the wireless electronic communication complies with at least one of a Bluetooth Low Energy (BLE) wireless protocol, a near field communication (NFC) protocol, or a radio-frequency identification (RFID) protocol.

In some embodiments, the predetermined characteristic of the output signal includes a bit rate or a symbol transmission rate, and the output signal includes data encoded according to the bit rate or a symbol transmission rate.

In some embodiments, the method further comprises varying the bit rate in a sequence that generates the code, wherein the varied bit rate creates a pattern that is recognized by the remote electronic computing device and identified to represent a unique identification that is acceptable for pairing.

In some embodiments, the bit rate or the symbol transmission rate is processed for encoding the data instead of data in a plurality of advertising packets exchanged between the remote electronic computing device and the medical apparatus by the medical apparatus including a processor and a memory that executes and stores, respectively, a custom Bluetooth Low Energy (BLE) stack including a unique profile that matches a profile stored on the remote electronic computing device.

In some embodiments, the predetermined characteristic of the output signal includes a signal strength of the output signal, and the output signal includes data encoded according to a modulated received signal strength indicator (RSSI) that is output to the remote electronic computer device.

In some embodiments, the method further comprises configuring the medical apparatus to include an electronic pairing device that processes an external event that changes a current state of the medical apparatus to a state that initiates the pairing.

In another aspect, a method for wireless electronic communication between a medical apparatus and a remote electronic computing device, comprises configuring the medical apparatus to include an electronic pairing device; receiving by the electronic pairing device an external event that changes a current state of the medical apparatus to a state that authorizes a secure pairing and authentication operation with a remote electronic computing device; and outputting by the medical apparatus a signal that facilitates the secure pairing and authentication operation with the remote electronic computing device.

In some embodiments, the electronic pairing device of the medical apparatus includes a near field communication (NFC) device and the method further comprises executing the NFC device to share data with the remote electronic computer device, wherein the data is secure due the NFC device exchanging an encryption key with the near field communication (NFC) device.

In some embodiments, the method further comprises forming a coupling between the medical apparatus and the remote electronic computer device; and modulating signals on a mutual capacitance, wherein the remote electronic computer device receives an AC coupled version of voltage pulses generated at the medical apparatus, which are decoded into the data.

In some embodiments, the electronic pairing device of the medical apparatus includes a voice recognition sensor that receives as the external event voice sounds captured by the remote electronic computer device, wherein the method further comprises converting the captured voice sounds into electronic signals for output to the medical apparatus; and instructing the medical apparatus via voice commands to accept a pairing request from the mobile device.

In some embodiments, at least one of the electronic pairing device of the medical or the remote electronic computer device employs an audible emission that includes encoded data.

In some embodiments, each of the electronic pairing device and the remote electronic computer device includes an inertial measurement unit that detects a force when the medical apparatus in communication with the remote electronic computer device and detected signals in each inertial measurement unit match to confirm a pairing with respect to a pairing attempt of at least one of the pairing and authentication operation.

In some embodiments, at least one of the electronic pairing device includes at least one light emitting device such as an LED or the like and one or more sensors of electromagnetic radiation of the at least one light emitting device that facilitates at least one of the pairing and authentication operation.

In another aspect, a medical apparatus comprises a controller that encodes data in an output signal according to a predetermined characteristic of the output signal and establishes a pairing with a remote electronic computing device including the encoded data in the output signal; and an electronic pairing device that receives an external event for changing a current state of the medical apparatus to a state that authorizes a secure pairing and authentication operation with the remote electronic computing device.

In some embodiments, at least one of the electronic pairing device includes an inertial measurement unit that that detects a force in the medical apparatus that when detected triggers a pairing attempt of the at least one pairing and authentication.

In some embodiments, when coupled together at least one of the electronic pairing device detects an orientation of the medical apparatus and/or the remote electronic computer device, and that records a change in the orientation to generate an encryption key for at least one of the pairing and authentication.

In some embodiments, at least one of the electronic pairing device of the apparatus and an inertial measurement device of the remote electronic computing device detects a tactile force of a coupling of the medical apparatus fand remote electronic computing device for purposes of at least one of pairing and authentication. The tactile force can be a shake, tap, squeeze, or other physical interaction with the medical apparatus.

In another aspect, a medical apparatus comprises a controller that encodes data in an output signal according to a predetermined characteristic of the output signal and establishes a pairing with a remote electronic computing device including the encoded data in the output signal; and an electronic pairing device that receives an external event for changing a current state of the medical apparatus to a state that authorizes a secure pairing and authentication operation with the remote electronic computing device.

Certain embodiments are described further in the following description, examples, claims and drawings. These features of embodiments will become more apparent from the following detailed description when taken in conjunction with the accompanying exemplary drawings.

BRIEF DESCRIPTION OF THE DRAWINGS

Various aspects of the invention and its embodiment are better understood by referring to the following detailed description. To understand the invention, the detailed description should be read in conjunction with the drawings, in which.

Figure 1:
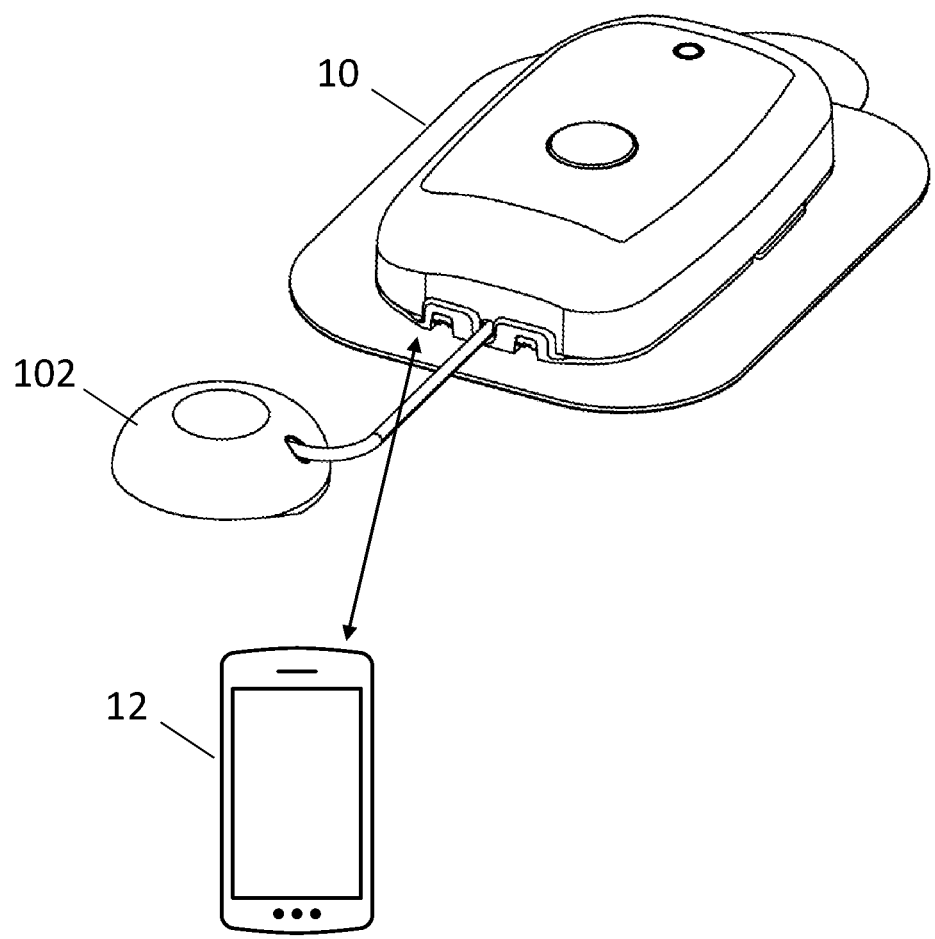
FIG. 1 is a schematic depiction of a medical pump system, in accordance with some embodiments.

The drawings are intended to illustrate certain exemplary embodiments and are not limiting. For clarity and ease of illustration, the drawings may not be made to scale, and in some instances, various aspects may be shown exaggerated or enlarged to facilitate an understanding of particular embodiments.

DETAILED DESCRIPTION

A wireless communication medium is required for a data exchange between a medical device and a remote electronic device, such as a user's smartphone, a custom or third party controller, continuous glucose monitor, and so on. Examples of a medical device may include medical pump embodiments and their associated methods and accessories to which the suitable devices and methods discussed herein may be applied may include those discussed in commonly owned U.S. patent application Ser. No. 15/122,132, filed Aug. 26, 2016, by P. DiPerna, titled "Fluid Delivery Pump," U.S. Pat. No. 16,028,256, filed Jul. 5, 2018, by P. DiPerna et al., titled "Medical Pump with Flow Control," U.S. patent application Ser. No. 16/520,521, filed Jul. 24, 2019, by P. DiPerna et al., titled "Subcutaneous Access Hub with Multiple Cannula Ports," U.S. patent application Ser. No. 15/122,132, Publication No. US 2016/0361489 A1, filed Mar. 3, 2015, by P. DiPerna, titled "Fluid Delivery Pump", and U.S. patent application Ser. No. 17/111,402, filed Dec. 3, 2020, and titled "Training Cartridge for Medical Pump Systems," each of which is incorporated by reference herein in its entirety.

In some embodiments, the wireless electronic communication medium complies with the Bluetooth™ Low Energy (BLE) wireless protocol area network technology, but is not limited thereto. Regardless of wireless communication medium, it is desirable for a medical apparatus such as an insulin pump to be connected to a remote electronic device, e.g., a smartphone, medical device controller, or the like, in a secure manner to allow useful and safe data transfer for patient privacy and secure control of the pump. Forming such a network connection in a safe and secure manner by a wireless electronic communication process commonly known as "pairing" permits the pump and remote electronic device to exchange data, for example, data including results collected by the pump.

Broadly speaking, wireless pairing occurs in a variety of ways. By way of example, BLE technology has three pairing options: Passkey Entry, Just Works, and Out-of-Band ("OOB").

Passkey Entry requires that the user enters data to securely pair, which may be of little use to patients with no access terminal or any understanding of the pairing process with no means for patient data entry and no display. Just Works™ pairing or the like has limited security and is therefore probably not an option for use with the pump. The third option, Out-of-Band pairing (OOB), represents the most secure option by completing the pairing process and encryption key exchange entirely out of band. This may take place in any method aside from the primary communication channel. Desirable characteristics of this option may include minimizing the potential for third parties to eavesdrop on the encryption key transfer and ensuring that only authorized devices can initiate the pairing process. Regardless of pairing options, since a pump employing BLE transmits or "advertises" identity information, it is important to ensure that this information is secure and safe from malicious access.

In brief overview, embodiments of the present inventive concepts incorporate one or more techniques for data hiding, secure pairing, and/or authentication, while complying with a wireless communication protocol such as BLE.

Referring generally to FIG. 1, a medical pump system is shown that includes a medical apparatus, for example, a pump 10, and a remote mobile device 12, such as a user's smartphone, a custom or third party controller, continuous glucose monitor, or the like configured to wirelessly exchange data with each other in a secure manner. It should be noted that in many cases, the embodiments of the pump 10 discussed herein may be operated directly by medical professionals that are treating patients. In many cases, the medical apparatus embodiments discussed herein may also be operated directly by individual end users that suffer from a particular medical condition, such as diabetes. Such individual end users may be using such pump embodiments to administer non-therapeutic fluids or therapeutic fluids such as saline, antibiotics, dextrose solutions, pain medications, peptides, and the like. Some therapeutic fluids that may be delivered by the medical pump system embodiments discussed herein may include therapeutic fluids used for the treatment of diabetes as well as other related medical conditions.

The remote mobile device 12 may include a processor and memory for executing and storing a software application that exchanges data with the medical pump 10, and includes a user interface that displays data received from the medical pump 10 and permits a user to enter information for output to the pump 10. For example, the pump 10 may include a patient port 102 or the like for exchanging fluids with a patient's body. Information regarding a fluid communication may be exchanged with the remote mobile device 12. For example, the remote mobile device 12 can output command data to the pump 10 to control an amount of insulin to be output via the patient port 102 into the patient's body. In another example, the remote mobile device 12 may receive temperature, blood pressure, or other medical information collected from sensors of the pump 10.

Prior to a data exchange between the pump 10 and remote mobile device 12, the pump 10 and remote mobile device 12 must be wirelessly paired. In wirelessly pairing the mobile device 12 and the pump 10, Bluetooth™ or other wireless technology is executed by the pump 10 and mobile device 12 that includes the transmission of advertising packets that include information that allow other devices to connect, but can also provide information about a device, such as data collected by the pump 10.

Figure 2:
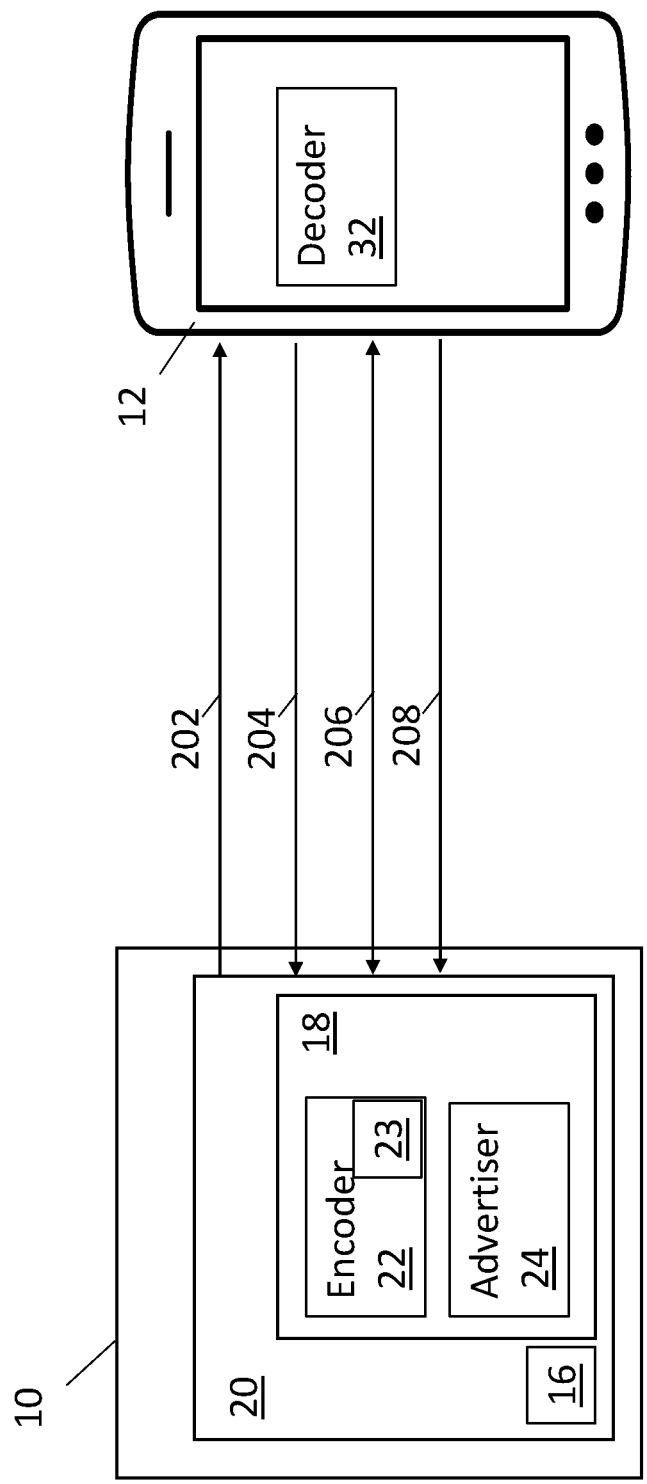
FIG. 2 is a block diagram of the medical pump system of FIG. 1, including components of a medical pump and mobile electronic device of the system and a communication exchange therebetween, in accordance with some embodiments.

In some embodiments, as shown in FIG. 2, the pump 10 includes a controller 20. The controller 20 may include a computer processor 16 such as a microprocessor and memory 18 as well as any suitable components that may be useful for interfacing with various elements of the pump 10. Such components may include electrical contacts, electrical conduits such as wiring, as well as drivers and any other instructions stored in the memory 18 that may facilitate use of the medical pump 10. This allows the controller 20 to monitor ambient temperature, ambient atmospheric pressure, and other information that may be of interest to a user of the mobile device 12.

In establishing a pairing between a medical pump and a remote mobile device such as a smartphone, keys are established which can then be used to encrypt a link, verify signed data, or perform other authentication functions. As shown by flow arrow 202, the pump 10 outputs (202) one or more advertising packets generated by the advertising packet generator 24 for response by the mobile device 12. The advertisement packets are transmitted and typically encoded to provide a level of security with respect to communication between the pump 10 and the mobile device 12. When the mobile device 12 responds (204), a handshake (bonding) is formed (206), facilitating a confirmed transfer (208) of data to the mobile device 12. The mobile device 12 can in turn display the data, output the data to another device, such as a cloud computing environment, remote database, or perform other operations on the received data.

Also stored in the memory 18 and executed by the processor 16 of the controller 20 may include a special-purpose encoder 22 and an advertising packet generator 24. As described herein, the encoder 22 executes a different encoding means such as bit rate than the data contained in the advertising packet. Accordingly, the encoder 22 includes a data hiding processor 23 for encoding symbols, etc. in a particular manner according to the bit rate at which an advertising packet is transmitted at step 202. The data hiding processor 23 may be a type of electronic pairing device that is implemented in hardware, software, firmware, or a combination thereof. The mobile device 12 includes a special-purpose decoder 32 at step 204 is constructed and arranged to receive and decode the advertising packets from the pump's encoder 22.

In some embodiments, in addition to transmitting and encoding advertising packets, the controller 20 can vary the bit rate in a sequence that generates the code. Therefore, the actual packets of encrypted data are not required as the critical component of providing security but rather the process of delivering in a varied bit rate which creates a pattern that can be recognized by the connecting device 12 and identified to represent a unique identification (ID) that is acceptable for pairing.

Figure 3:
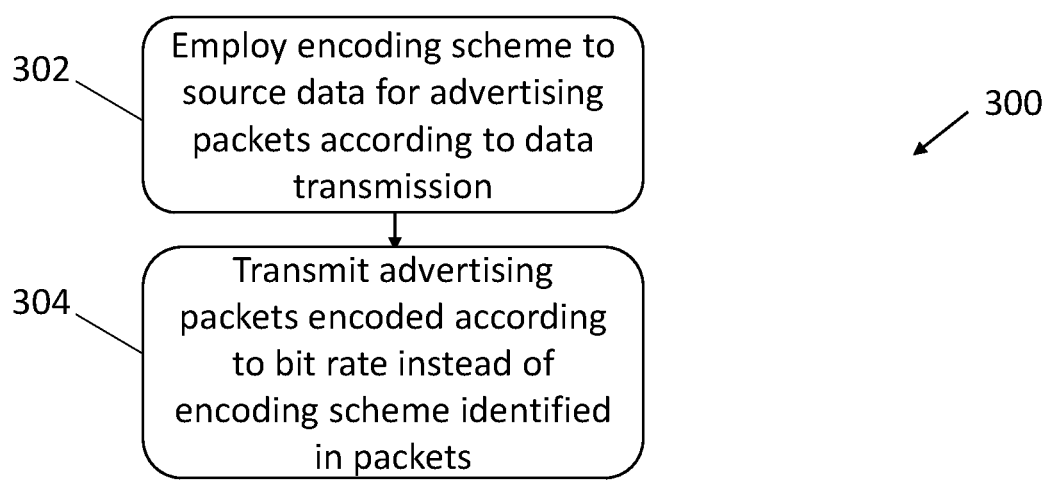
FIG. 3 is a flow diagram of an embodiment of a method for data hiding in a pairing exchange between a medical pump and mobile electronic device, in accordance with some embodiments.

FIG. 3 is a flow diagram of an embodiment of a method 300 for data hiding in a pairing between the medical pump 10 and mobile electronic device 12 of the medical pump system of FIGS. 1 and 2, in accordance with some embodiments. At least some of method 300 can be executed by an electronic pairing device of the controller 20 that is implemented in hardware, software, firmware, or a combination thereof.

At block 302, the pump 10 employs an encoding scheme to the advertising packets formed by the advertising packet generator 24. For some embodiments, the controller microprocessor 16 may include a low power consuming high performance microprocessor that executes code according to BLE, near field communication, and the like.

As is well-known, an advertising packet in accordance with the BLE wireless protocol includes information that allows other devices such as the mobile device 12 to connect, but can also provide information about a device. However, instead of using the data in the advertising packet for encoding the data, e.g., encryption keys, etc., the data for transmission is encoded according to the bit rate, symbol transmission rate, or other type of data transmission is used. Thus, at block 304, transmitted advertising packets are encoded according to the bit rate instead of encoding scheme identified in the packets. For example, an advertising packet that is transmitted at 1 Mbit/s is encoded with a '0' value, and when transmitted at 2 Mbit/s is encoded with a '1' value. Accordingly, the transmission of advertising packets is itself employed as a data hiding technique, in particular, in the exchange secret or sensitive data, encryption keys, identification, and so on.

For example, an advertising packet includes a URI type field that identifies a UTF-8 encoding scheme. Nevertheless, the system relies on the bit rate to encode the data. Here, a custom BLE protocol stack may be implemented for execution by the device with a unique profile that matches that on the intended connected device. This ensures that both the host and controller operate with an aligned interface to drive and manage the secure connection and data transfer. The pump does not connect to any BLE device but rather communicates via a custom application or proprietary device, e.g., controller, compatible blood glucose meter, with compatible firmware, hardware, software, or a combination thereof, to support the connection and data communication.

Figure 4:
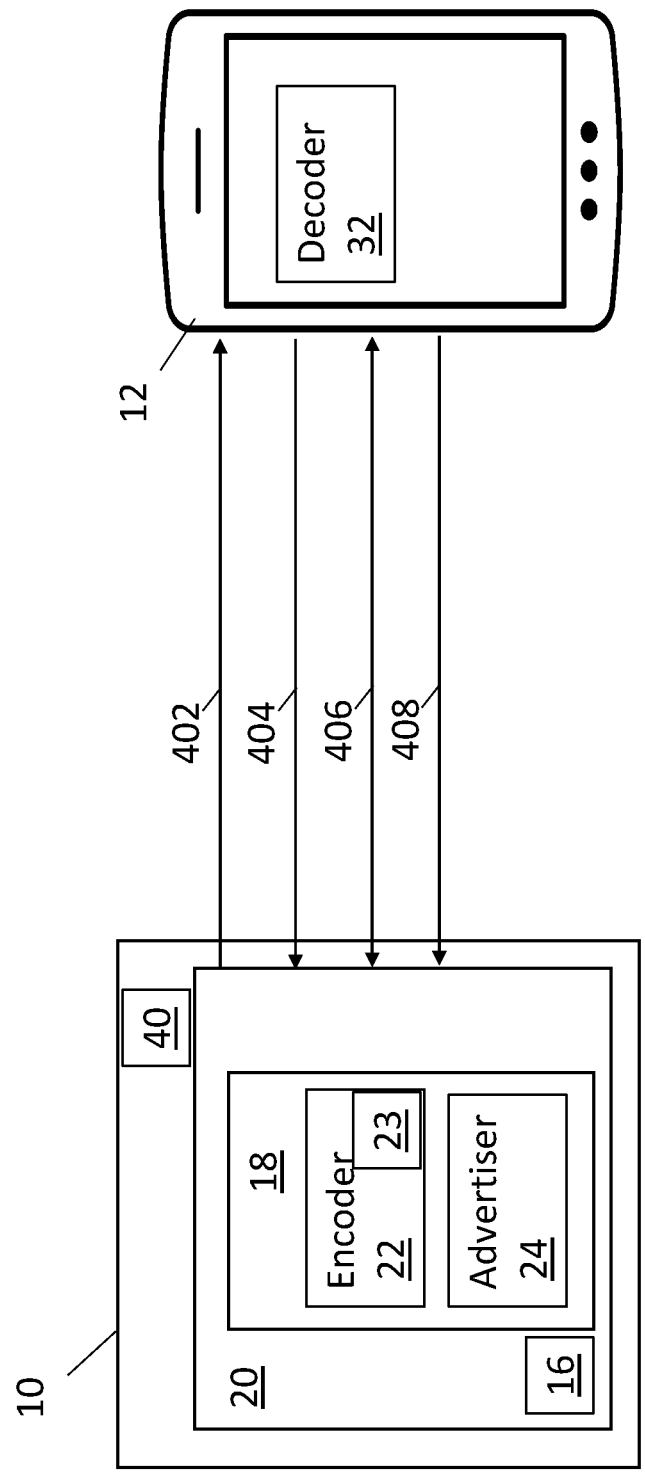
FIG. 4 is a block diagram of a medical pump system including components of a medical pump and mobile electronic device of the system and a communication exchange therebetween, in accordance with other embodiments.

Referring to FIG. 4, in other embodiments, the medical pump 10 can output (402) a modulated received signal strength indicator (RSSI), or a measurement of the power present in a radio signal expressed in dBm or decibels relative to milliwatts of received power, in the advertising packet. In this embodiment, the controller 20 includes an RSSI modifying element that includes a signal modification module 40, for example, formed of electrical circuits and/or software that controls the signal strength transmitted by the pump 10, e.g., the signal strength of a received wireless signal, for example, a radio frequency (RF) signal. The mobile device 12 operating in a BLE scanning state can receive advertising packets from the pump 10 including an RSSI distance estimation value. The output power is not known to the receiver 10 so the output power information may be included in the advertising packet. The encoder 22 of the pump controller 20 can encode the data in this signal to arbitrary bit depths, limited only by the noise in the RSSI on the receiving device 12. For example, changing the transmit strength from 0 dBM to −20 dBm can signify a '0' followed by a '1', or the direction of change could itself encode a '0', for example, similar to a Manchester encoding format. When the mobile device 12 responds (404), a handshake (bonding or pairing) is formed (406), facilitating a confirmed transfer (408) of data to the mobile device 10.

Figure 5:
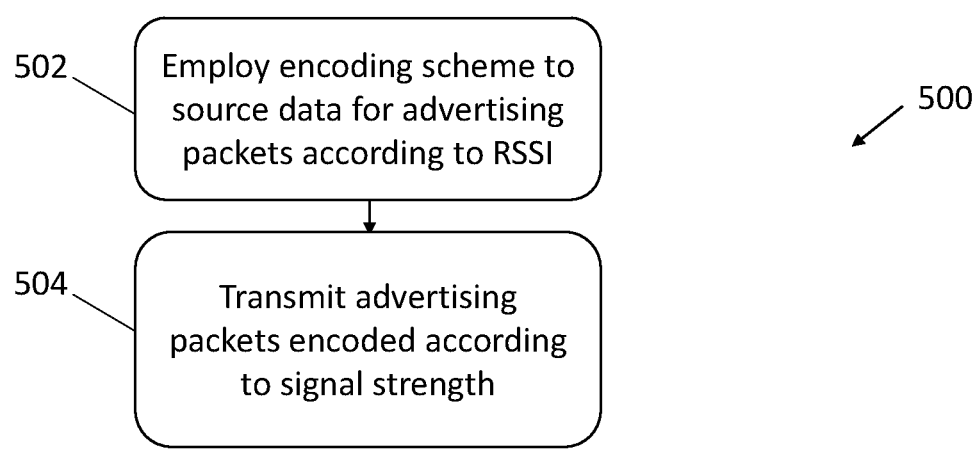
FIG. 5 is a flow diagram of an embodiment of a method for data hiding in a pairing exchange between the medical pump and mobile electronic device of the medical pump system of FIGS. 1 and 4, in accordance with some embodiments.

FIG. 5 is a flow diagram of an embodiment of a method 500 for data hiding in a pairing between the medical pump 10 and mobile electronic device 12 of the medical pump system of FIGS. 1 and 2, in accordance with some embodiments. At least some of method 500 can be executed by an electronic pairing device of the controller 20 that is implemented in hardware, software, firmware, or a combination thereof.

At block 502, the pump 10 employs an encoding scheme to advertising packets formed by the advertising packet generator 24. An advertising packet in accordance with the BLE wireless protocol contain information can include an RSSI distance estimation value. However, the data hiding processor 23 processes an RSSI signal altered by the signal modification module 40 to provide at block 504 an encoding scheme based on the signal strength, for example, changing the transmit strength from 0 dBM to −20 dBm can signify a '0' followed by a '1', or the direction of change could itself encode a '0'. Accordingly, the transmission of advertising packets is itself employed as a data hiding technique, in particular, in the exchange secret or sensitive data, encryption keys, identification, and so on.

Figure 6:
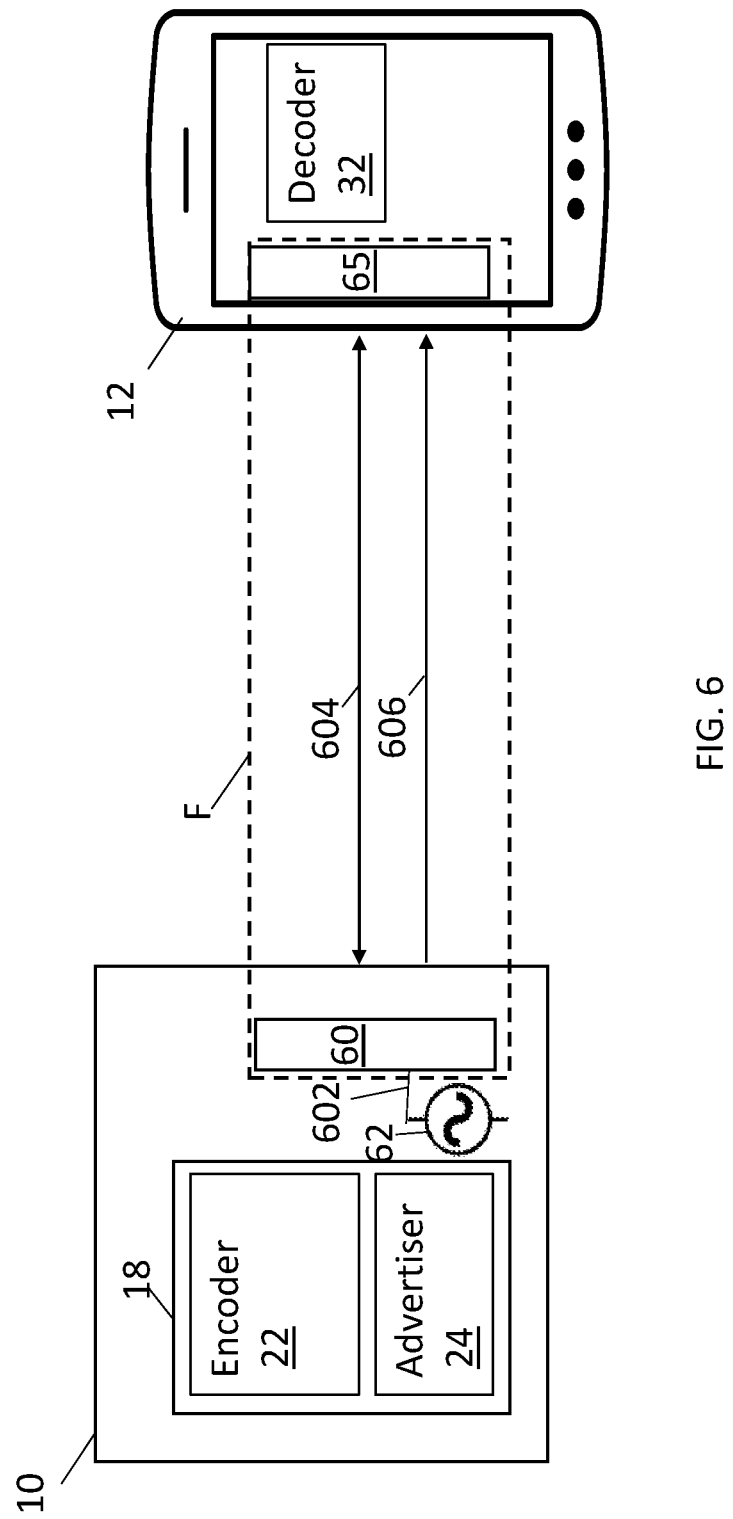
FIG. 6 is a block diagram of a medical pump system employing a capacitive, inductive, or otherwise near field communication (NFC) system as part of a pairing operation, in accordance with other embodiments.

Referring to FIG. 6, in other embodiments, data can be exchanged via an inductive or otherwise near field communication between a medical pump 10 and a mobile device 12 such as a smartphone or the like, offering a low-power, proximity-mediated alternative to existing wireless communication techniques. The medical pump 10 can include an electronic pairing device, namely, an RF near field communication device 60, which can be instructed and arranged to share data including secret or private data such as encryption keys and/or other information used to generate encryption keys. The RF near field communication device 60 can be formed of electronic circuits and/or software stored in a memory 18 and executed by a hardware processor 16 of the pump 10 to provide a near field channel between the pump 10 and the mobile device 12. In some embodiments, the RF near field communication device 60 is implemented as an inductive loop, for example, tuned to a predetermined frequency such as 125 kHz, 13.56 MHz, and so on, but not limited thereto. In some embodiments, the RF near field communication device 60 generates an electronic communication according to a well-known technical standardized protocol such as radio-frequency identification (RFID) or NFC. In other embodiments, the RF near field communication device 60 communicates with the mobile device 12 in accordance with a custom protocol that is an alternative to RFID or NFC, such as a pulse-based communication, Manchester-encoded information, amplitude, or frequency modulated signals, and so on. The data hiding processor 23 applies an encoding scheme with respect to data exchanged by the RF near field communication device 60. In cases where NFC provides a data exchange, a temporary key is communicated during a pairing process, which is required by the BLE device. However, NFC lacks security features against eavesdropping or the like. The NFC pairing process shown in FIG. 6 can provide security generally lacking in NFC by including a proprietary technique of modulating frequency. Here, a form of inductive coupling can occur.

To perform capacitive coupling, each of the pump 10 and the mobile device 12 includes a conductive electrode element, for example, a metal plate, in order to form a capacitive coupling in which the pump 10 and the mobile device 12 communicate by modulating signals on a mutual capacitance. A voltage source 62 can apply voltage pulses (602) to the metal plate 60 or related electrode of the pump 10, also referred to as a transmitter electrode. The mobile device 12 likewise includes a capacitive electrode 65, for example, a metal plate. In some embodiments, as shown in FIG. 6, the mobile device electrode 65 is internal to and part of the device 12. In other embodiments, the mobile device electrode 65 is removably coupled to the housing of the mobile device 12 to be in use only for communication with the pump 10.

When the pump 10 and mobile device 12 are positioned so that they are proximal each other, i.e., their respective electrodes 60, 65 are proximal and substantially parallel so as to permit the formation of an electric field (F) therebetween, the mobile device 12 may receive (604) an AC coupled version of the pump-generated voltage pulses. These voltage pulses (604) may be decoded by the mobile device's decoder 32 into communication data.

For example, the pump controller 20 may include a pulse-width modulation module or other hardware and/or software that generates the signals for transmitting data to the mobile device via the electric field (F). The near field communication can establish secure channels and use encryption when sending sensitive data (606), for example, between the two RFID or NFC-enabled devices 10, 12.

Figure 7:
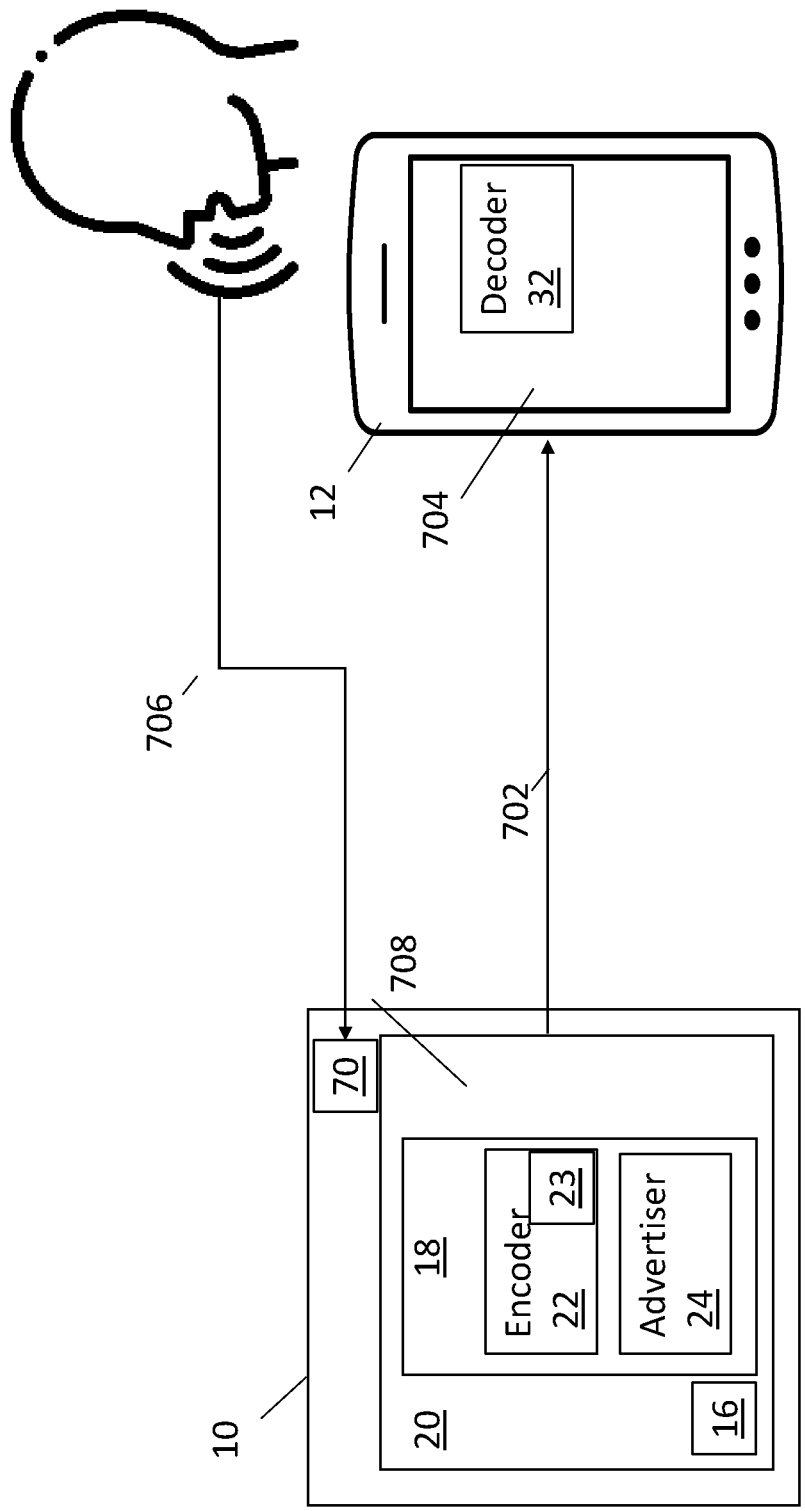
FIG. 7 is a block diagram of a medical pump system employing voice recognition as part of a pairing operation, in accordance with other embodiments.

Referring to FIG. 7, in other embodiments, a medical pump 10 can include one or more voice recognition sensors 70, such as a microphone or other acoustic detector and associated processors, which may be another type of electronic pairing device, and can be constructed and arranged to receive voice captured by the mobile device 12 and converted into electronic signals for output to the pump 10, and in doing so, can instruct the pump 10 via voice commands or the like to accept a pairing request from the mobile device 12. In other embodiments, the data hiding techniques described in FIGS. 3-5 can be executed by the pump 10 shown in FIG. 7. For example, voice-related features can be added to other forms of code exchanges or device recognition.

The pump 10 can output from a generating device 72 a keyword or phrase (702) to the mobile device 12, which is then displayed (704) on a user interface of the mobile device. The mobile device user utters (706) the displayed keyword or phrase, which is detected by a voice recognition sensor 70 of the pump 10. Upon detecting (708) that the keyword or phrase has been spoken, the pump controller 20 can determine that the user is in sufficient proximity and has control of the device 12.

In some embodiments, the voice recognition sensor 70 recognizes the identity of the speaker. Here, when a patient first receives the pump 10, the patient may be required to participate in a training program or routine, during which the patient utters various words or phrases so that the pump 10 can collect sufficient data to subsequently match the user's voice to the voice captured when speaking (706) during a pairing operation.

Figure 8:
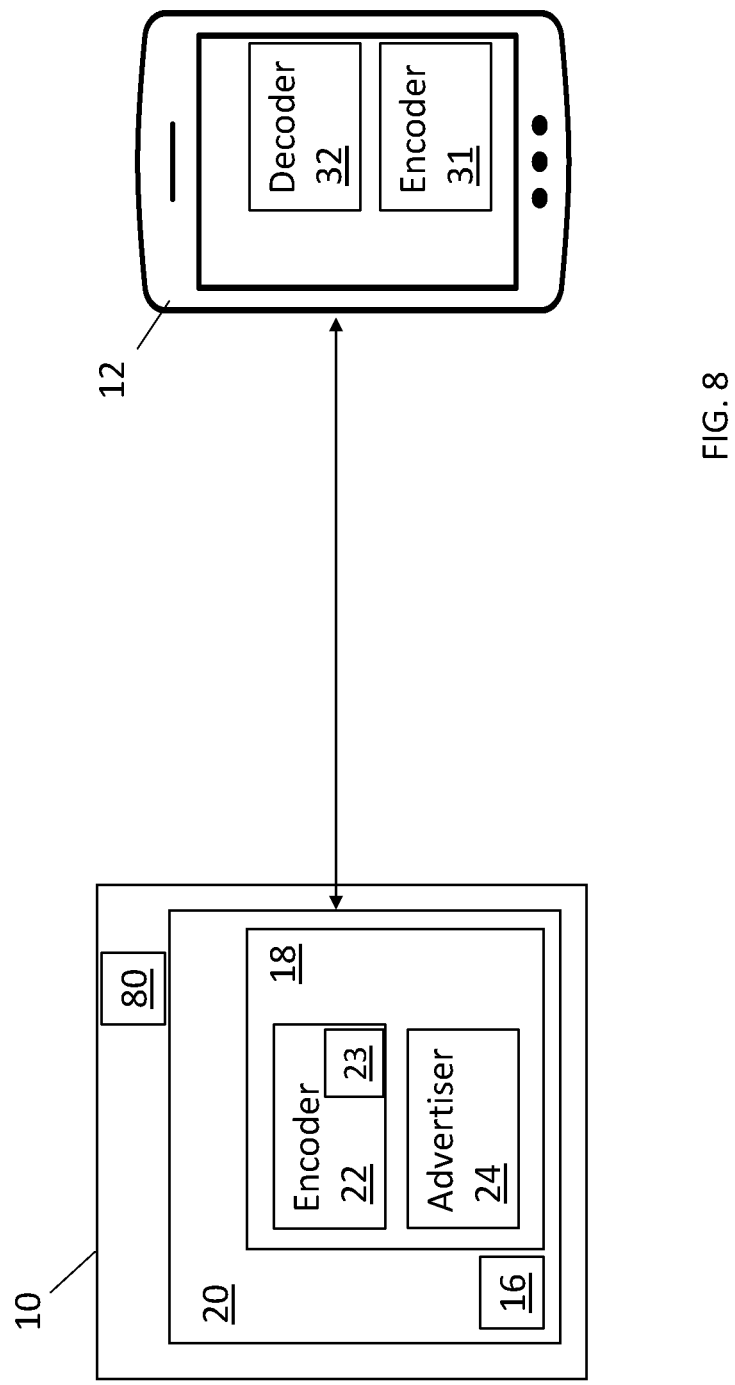
FIG. 8 is a block diagram of a medical pump system employing acoustic communications as part of a pairing operation, in accordance with other embodiments.

Referring to FIG. 8, in other embodiments, a medical pump 10 can include an electronic pairing device, namely, and audible processing device 80 that generates and outputs audible emissions such as tones, songs, or other audible waveforms. In some embodiments, the audible processing device 80 includes a tone generator but not limited thereto. In other embodiments, the mobile device 12 includes an audible generator (not shown) instead of the medical pump 10. In other embodiments, each of the pump 10 and the mobile device 12 includes audible device 80 and a receiver (not shown) for receiving and processing audible emissions from the other of the pump 10 and the mobile device 12.

In embodiments where the pump 10 controls the audible device 80 to emit a sound, the pump encoder 22 encodes the sound to include data and the mobile device 12 includes a decoder 32 that decodes the transmissions, for example, musical notes, rhythm, timing, frequency changes between adjacent notes, frequency modulation of a single note, volume, and/or other characteristic of an audible signal but not limited to. In embodiments where the mobile device 12 generates and emits a sound, the mobile device 12 includes an encoder 31 that encodes the sound to include data. This feature permits a user to listen to music, soothing sounds such as ocean waves, tropical rain forest, and so on while these sounds also contribute to a pairing process between the pump 10 and the mobile device 12.

In some embodiments, the audible device 80 generates acoustic communication signals that are outside the audio frequency range that can be heard by the human ear, e.g., 20 Hz to 20,000 Hz. For example, the audible device 80 can include an electronic device that provides ultrasonic emissions, chirps, or the like. In some embodiments, one of the pump 10 and the mobile device 12 can generate ultrasonic sounds, or other emissions inaudible to humans, that is received by the other of the pump 10 and the mobile device 12. For example, the pump 10 or mobile device 12 may employ a special-purpose ultrasonic receiver or capacitive pressure sensor, and the other of the pump 10 or mobile device 12 employs a speaker or piezo disc or other emitter, e.g., part of audible device 80, for generating ultrasonic signals. Data is encoded in an audio signal by the pump 10 transmitting a high frequency signal, e.g., whistling a variable frequency, which can be interpreted by the intended receiving device 12 to provide a level of security and ensure that the appropriate devices are paired.

Figure 9:
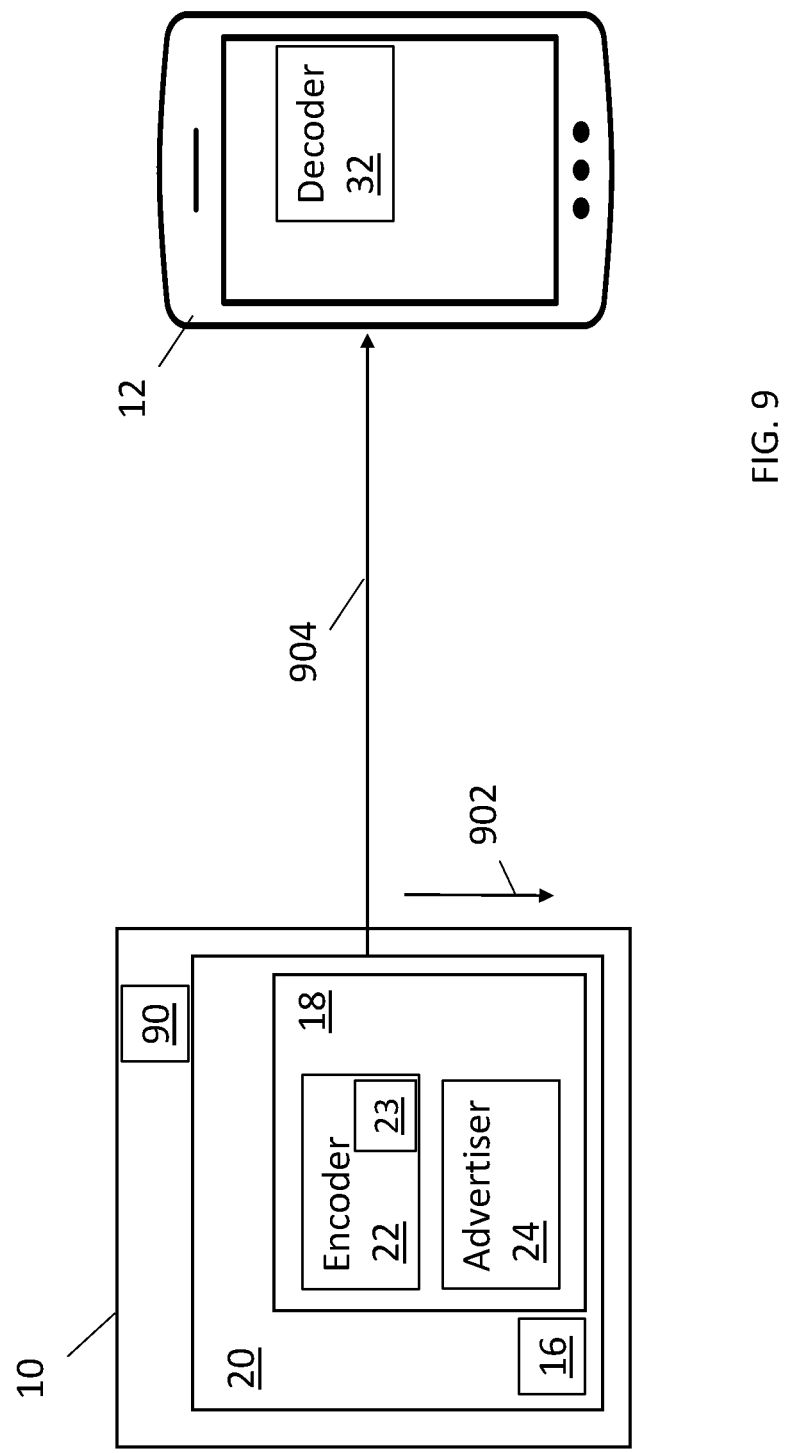
FIG. 9 is a block diagram of a medical pump system employing gravity sensing devices as part of a pairing operation, in accordance with other embodiments.

Referring to FIG. 9, in other embodiments, a medical pump 10 can include special-purpose sensor 90 such as an accelerometer or inertial measurement unit as yet another type of electronic pairing device that detects when the pump 10 experiences an unexpected, sudden, or other movement that is determined to be out of the ordinary. When the pump 10 is in free fall or other sudden acceleration (902), e.g., the x, y, and z axes of a Cartesian coordinate arrangement) are measured by the sensor 90 at 0 g values, the pump 10 can output (904) a pairing request to the mobile device 12. The device 12 intended to be connected to the pump 10, e.g., a smartphone with software application when executed is in a pairing mode, so that the device 12 expects to receive a confirmation from the pump 10 that it has be subjected to the "freefall" behavior.

Figure 10:
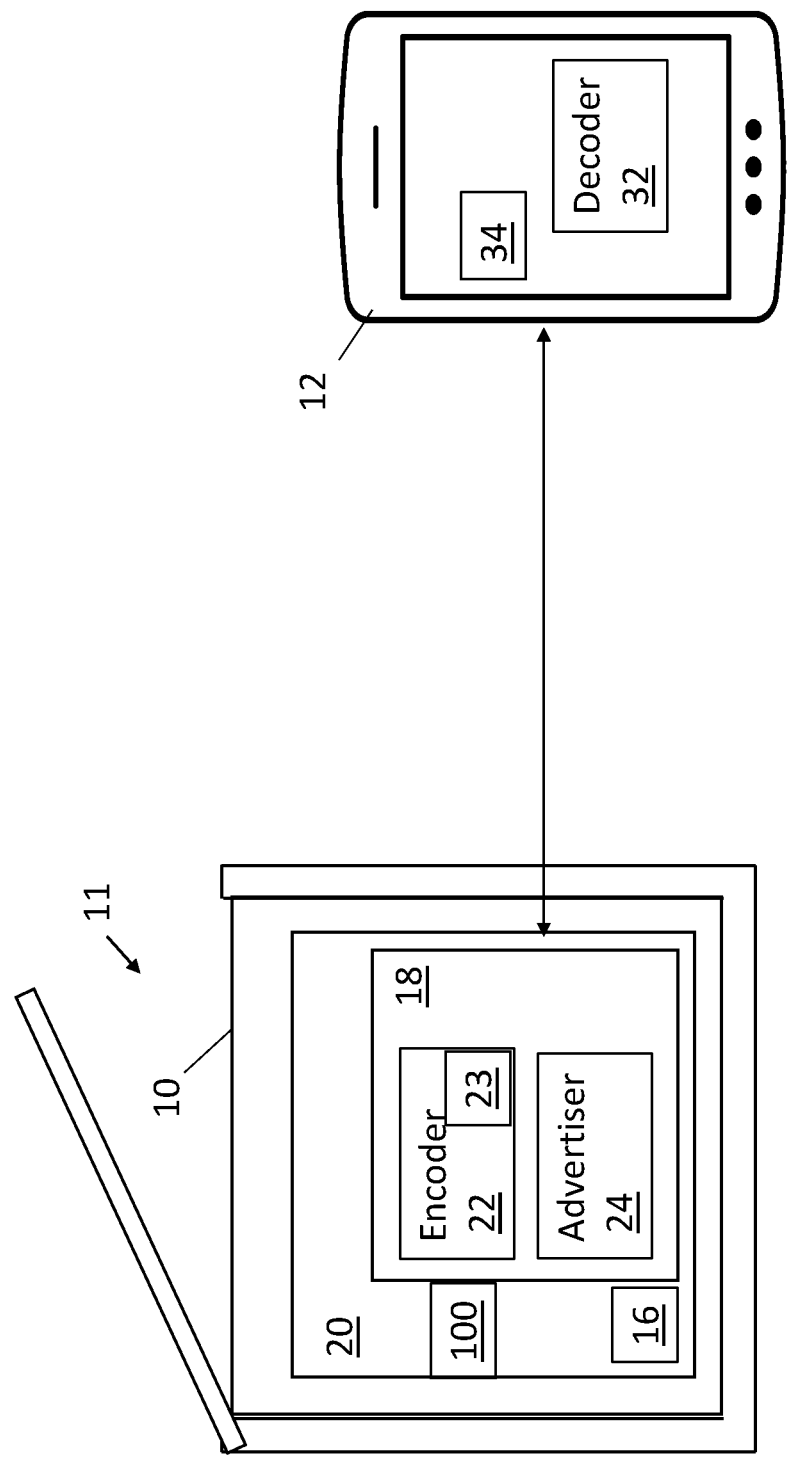
FIG. 10 is a block diagram of a medical pump system employing light sensors as part of a pairing operation, in accordance with other embodiments.

Referring to FIG. 10, in other embodiments, a medical pump 10 relies on a change in an ambient lighting condition to exchange data related to a pairing operation. Here, the pump 10 can employ one or more light sensors 100 such as reverse-biased LEDs or the like to permit the pump 10 to detect when the pump 10 is enclosed or otherwise positioned in a special shipping package 11. For example, if the shipping package 11 containing the pump 10 blocks a certain wavelength of light, then when the photo detector detects that wavelength of light for the first time after it was blocked, the pump 10 can temporarily accept pairing attempts. Although light sensors are described, other sensors that detect electromagnetic radiation in other sections of the electromagnetic spectrum, i.e., other than visible light, may equally apply.

In some embodiments, the pump 10 can store light wavelength characterization data in memory 18 or to characterize at run time via ambient light analysis, the wavelength response of one or more reverse biased LEDs 100. Then, in the pairing process, the pump 10 could turn on those LEDs 100. A camera 34 on the device 12 could be directed at the LEDs 100 to establish an electronic communication and/or other exchange of electromagnetic signals. The device 12 could then characterize the spectrogram of light produced by the LEDs, and transmit this information to the pump 100, thereby demonstrating that the device 12 is in close proximity to the pump 10 at that time.

Figure 11:
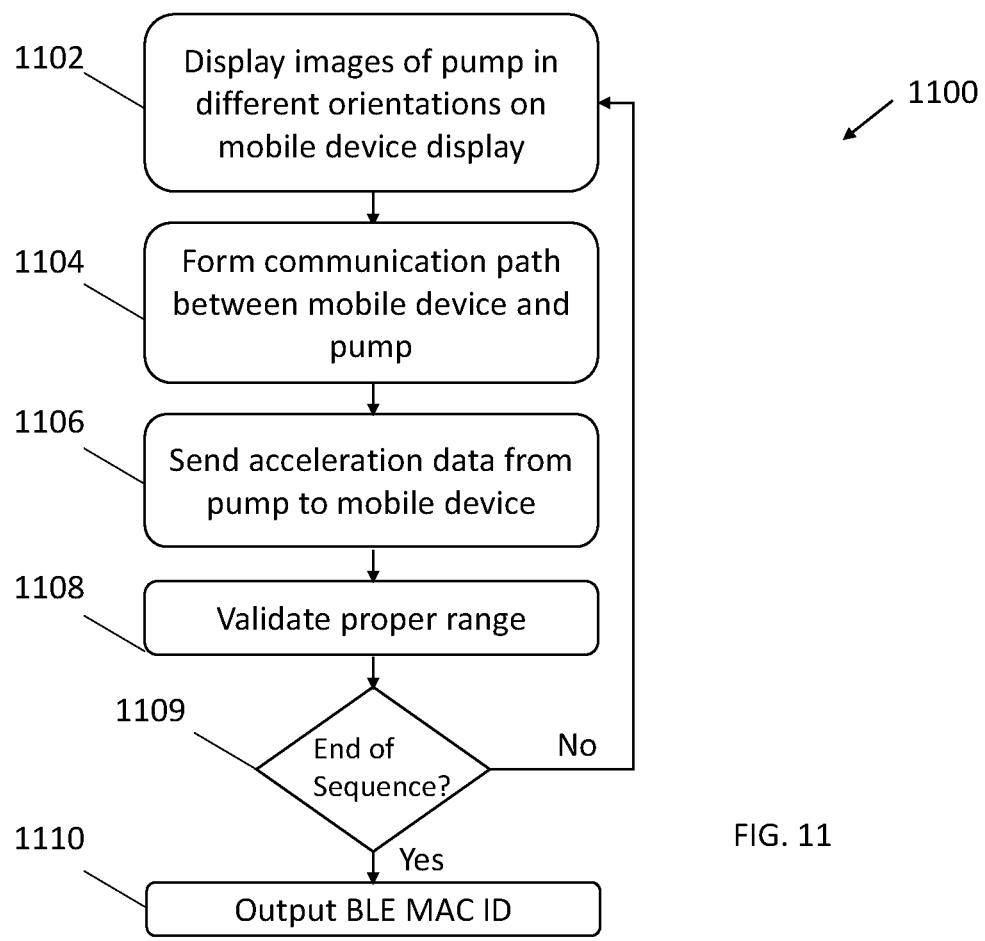
FIG. 11 is a block diagram of a medical pump system, in accordance with other embodiments.

Referring to FIG. 11, in other embodiments, the mobile device 12 can include hardware and/or software, for example, an accelerometer, to instruct a user to change an orientation of the mobile device 12. This can be achieved, for example, by displaying an image or other representation of the pump in desired orientations, for example, orientations determined to result in an electronic communication between the pump 10 and device 12 that includes a pairing. In response, the user can orient or otherwise move the pump 10 according to the instruction to match the displayed orientation of the pump. In some embodiments, the pump 10 can include an RF near field communication device, for example, shown and described with reference to FIG. 6, and the user can orient the pump 10 to match the displayed representation. By combining this feature with a near field communication means, the accelerometer data could be sent from the pump 10 to the device 12 as part of out-of-band pairing.

The method 1100 shown in FIG. 11 can therefore be executed by the system shown in FIG. 6. Other embodiments permit the method 1100 to be performed on a medical pump system illustrated in other figures herein that perform a pairing operation.

At block 1102, an application stored at and executed at the mobile device 12 can display a series of predetermined graphics, pictures, or the like of the pump 10 in various orientations.

At block 1104, the user can hold the pump 10 up to the mobile device 12 to establish an electronic communication.

At block 1106, the pump 10 outputs accelerometer data including a current orientation to the mobile device 12. In some embodiments, the pump 10 outputs a current orientation as part of accelerometer data via an NFC communication to the device 12.

At block 1108, the mobile device application validates a proper range that is sufficient to complete an authorization process between the mobile device 12 and the pump 10. At decision diamond 1109, the method 1100 may return to block 1102, where different orientation in the displayed series of graphics, etc. is processed until an accelerometer reading is provided from the pump 10 to the mobile device 12 for each orientation in the displayed sequence.

At block 1110, after the entire sequence is processed and validated, the mobile device 12 could output its BLE MAC ID or similar identifying characteristic via an NFC communication to the pump 10, which stores it in a whitelist or other data storage arrangement.

The user may hold the pump 10 and device 12 together and randomly vary the orientation. Since both device 12 and pump 10 are experiencing the same change in orientation, they can use an inertial measurement unit, accelerometer, or similar to record those changes and use them to independently generate the same encryption key or seed for an encryption algorithm. This technique cannot be snooped on wirelessly as it is a purely physical sharing of data—both pump 10 and device 12 are experiencing the same orientations and feeding the changes in orientation, absolute orientation, or a post-processed representation of orientation into the same algorithm. In some embodiments, the remote device 12 sends a signal regarding a motion, change in force, or the like that is detected by a sensor of the remote device 12 and output to the pump 10. The controller 20 in response processes the received signal data and determines whether there is a match or other comparison result to facilitate a pairing operation. In some embodiments, authorization exchanges are made between the pump 10 and remote device 12 as part of or instead of the operation.

Two separate encryption keys could be generated as follow. When the user wants to pair a new device, the user can choose an option on the application, and then bring the device, i.e., pump 10, in contact with the remote electronic device 12 such as a mobile phone or other compatible device such as a blood glucose meter or continuous glucose monitoring system. The application can instruct the device that a new pairing is to be initiated by using NFC. When the LEDs flash a certain color pattern, the user separates the two and rotates the remote electronic device 12 and the pump 10 separately for a set amount of time in as many directions as possible. The more random this is, the quicker this phase will end. The pump and phone use their respective accelerometers to generate a random public key on each side and exchange them. The pump 10 has also used the second half of the accelerometer outputs to generate a random seed (a nonce). It will use this to generate a Confirmation Value. At this point the pump 10 will use some pattern to tell the user to bring the pump 10 and remote electronic device 12 in contact.

Using NFC, the pump sends the Confirmation Value and Nonce to an application stored at and executed by the remote electronic device 12 or related device. The application then uses the Nonce to generate a Confirmation Value. Both values should match. The application then sends its BLE MAC ID to the device to signify success, and the pump 10 adds the MAC to its whitelist.

Figure 12:
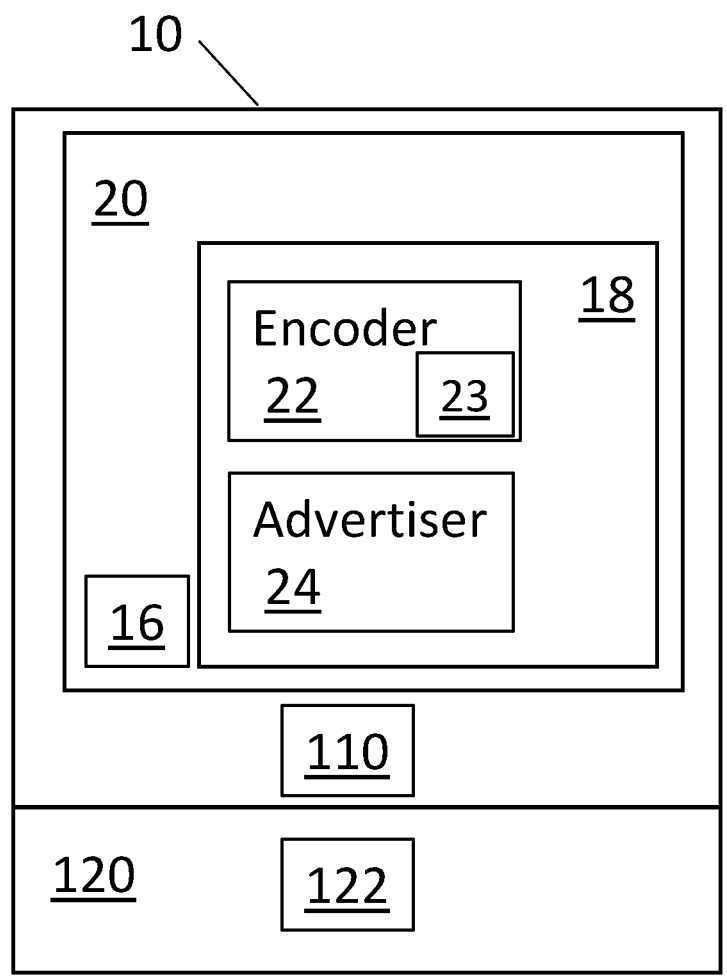
FIG. 12 is a block diagram of a medical pump system employing an inertial measurement unit as part of a pairing operation, in accordance with other embodiments.

Referring to FIG. 12, each of the pump 10 and remote electronic device 12 has an inbuilt accelerometer or other inertial measurement unit that can form a pairing when the tapping or shaking actions by one or both of the pump 10 and remote electronic device 12, which can be simultaneously measured by both the pump 10 and device 12, then used to demonstrate close proximity and thereby identity. For example, a shaking or tapping pattern can be detected simultaneously by an accelerometer or other inertial measurement unit that 122 built into a smartphone 120 as well as an inertial measurement unit 110 that one in the pump 10. If the pump 10 and phone 12 are in contact these patterns should be similar in phase to confirm they are the correct devices with intention of pairing together. For example, the user could place the pump 10 on top of the device 120, which in turn is positioned on a tabletop, then tap a pattern on the top of the pump 10. The particular tap timing or other characteristics such as duration, strength, vibration, etc., as measured by the underlying device 120 can be sent from the device 120 to the pump 10, where those characteristics could be correlated, e.g., by the accelerator 110 of the pump 10 taking measurements for comparison to those of the device 120, to determine whether the respective motions enacted on the device 120 and pump cause the measured signals to be in phase, or otherwise formed to have similar signal characteristics. Tapping or shaking detected by the pump 10 could also be used to instruct the user to confirm an intended action by the device 120 instructing, for example, "double tap the pump," followed by the pump 10 confirming to the device 120 that a double tap was detected. Upon such handshake, an action such as changing delivery rate could be enacted.

Figure 13:
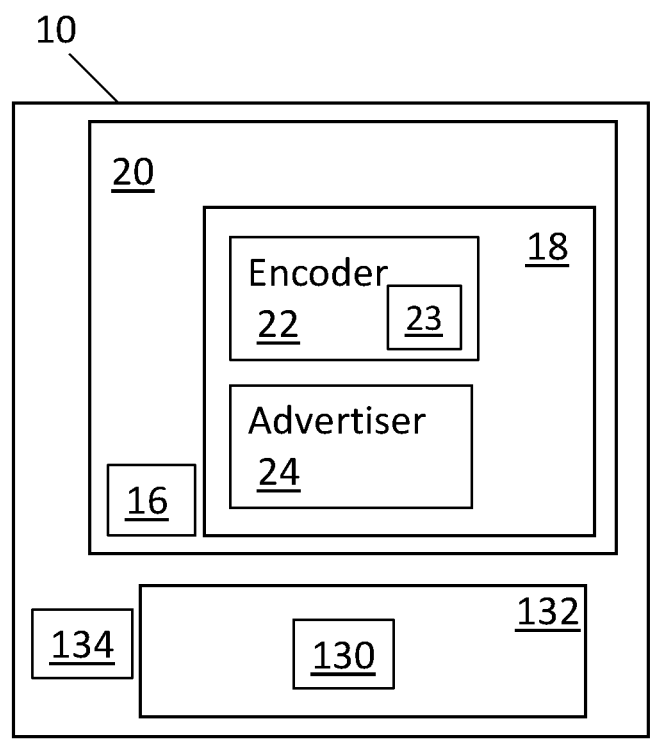
FIG. 13 is a block diagram of a medical pump system employing an atmospheric pressure sensor as part of a pairing operation, in accordance with other embodiments.

Referring to FIG. 13, in some embodiments the pump 10 includes an atmospheric pressure sensor 130 inside the pump 10. To confirm identity or to ask the user to confirm an intended action, a device 130 could instruct the user to squeeze the case. The atmospheric pressure sensor 130 may be positioned in a sealed or semi-sealed case 132 for monitoring the pressure of the ambient atmosphere. The pump's interior pressure is affected by the user squeezing the casing or could be detected by, for example, one or more strain gauges 134 attached to the case 132 or deposited throughout the body of the pump. In some embodiments, the sensor 130 can detect pressure changes in the air volume of the pump during a dispense cycle and may also include temperature measurement capabilities. Another example is the detection of small changes in the value of components such as capacitors that vary when squeezed or when pressure changes. The pressure sensor 130 is operatively coupled to the controller 20 which may be configured to monitor pressure measurements of the pressure sensor 130 from within the air volume of the fluid reservoir of the pump 10. The direction would come from a separate device such as a smartphone with a specific MMI application intended to compliment the pump 10. The squeezing is intended to provide an alternative method to input a passcode which is typically performed with a keypad or buttons. The passcode can include a pattern of short and long squeezes or a certain quantity of momentary squeezes, waiting direction from the application for an additional quantity. Predetermined tactile forces, such as a number of squeezes, e.g., 3-5 times, may be repeated to provide the passcode.

Embodiments illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation and use of such terms and expressions do not exclude any equivalents of the features shown and described or portions thereof, and various modifications are possible. The term "a" or "an" can refer to one of or a plurality of the elements it modifies (e.g., "a reagent" can mean one or more reagents) unless it is contextually clear either one of the elements or more than one of the elements is described. Thus, it should be understood that although embodiments have been specifically disclosed by representative embodiments and optional features, modification and variation of the concepts herein disclosed may be resorted to by those skilled in the art, and such modifications and variations are considered within the scope of this disclosure.

With regard to the above detailed description, like reference numerals used therein refer to like elements that may have the same or similar dimensions, materials, and configurations. While particular forms of embodiments have been illustrated and described, it will be apparent that various modifications can be made without departing from the spirit and scope of the embodiments of the invention. Accordingly, it is not intended that the invention be limited by the forgoing detailed description.

What is claimed is:

1. A method for wireless electronic communication between a medical apparatus and a remote electronic computing device, comprising:

generating and outputting by the medical apparatus an output signal, including encoding data in the output signal according to a predetermined characteristic of the output signal, including:
  outputting at least one advertising packet from the medical apparatus to the remote electronic computing device; and
  encoding the at least one advertising packet according to a data transmission characteristic of the predetermined characteristic of the output signal, the method further comprising:
receiving and decoding by the remote electronic computing device encoded data of the at least one advertising packet in the output signal; and
establishing a pairing between the medical apparatus and the remote electronic computing device in addition to transmitting device output data.

2. The method of claim 1, wherein the medical apparatus includes an insulin delivery pump or other medical device and the remote electronic computing device includes a user interface and an input/output computing element for operating and controlling the insulin delivery pump or other medical device.

3. The method of claim 1, wherein the wireless electronic communication complies with at least one of a Bluetooth Low Energy (BLE) wireless protocol, a near field communication (NFC) protocol, or a radio-frequency identification (RFID) protocol.

4. The method of claim 1, wherein the predetermined characteristic of the output signal includes a bit rate or a symbol transmission rate, and the output signal includes data encoded according to the bit rate or a symbol transmission rate.

5. The method of claim 4, further comprising: varying the bit rate in a sequence that generates the code, wherein the varied bit rate creates a pattern that is recognized by the remote electronic computing device and identified to represent a unique identification that is acceptable for pairing.

6. The method of claim 4, wherein the bit rate or the symbol transmission rate is processed for encoding the data instead of data in a plurality of advertising packets including the at least one advertising packet exchanged between the remote electronic computing device and the medical apparatus by the medical apparatus including a processor and a memory that executes and stores, respectively, a custom Bluetooth Low Energy (BLE) stack including a unique profile that matches a profile stored on the remote electronic computing device.

7. The method of claim 4, wherein the predetermined characteristic of the output signal includes a signal strength of the output signal, and the output signal includes data encoded according to a modulated received signal strength indicator (RSSI) that is output to the remote electronic computer device.

8. The method of claim 1, further comprising configuring the medical apparatus to include an electronic pairing device that processes an external event that changes a current state of the medical apparatus to a state that initiates the pairing.

* * * * *